United States Patent
Ebert et al.

(10) Patent No.: US 10,183,296 B2
(45) Date of Patent: Jan. 22, 2019

(54) ASSEMBLY, INSTRUMENT FOR PERFORMING A TEMPERATURE-DEPENDENT REACTION AND METHOD FOR PERFORMING A TEMPERATURE-DEPENDENT REACTION IN AN ASSEMBLY

(71) Applicant: Roche Molecular Systems, Inc., Pleasanton, CA (US)

(72) Inventors: Sven Ebert, Zurich (CH); Paul Federer, Wolhusen (CH); Thomas Schlaubitz, Meggen (CH); Stefan Vollenweider, Sins (CH); Urs Wittenwiler, Unteraegeri (CH)

(73) Assignee: Roche Molecular Systems, Inc., Pleasanton, CA (US)

( * ) Notice: Subject to any disclaimer, the term of this patent is extended or adjusted under 35 U.S.C. 154(b) by 0 days.

(21) Appl. No.: 15/693,009

(22) Filed: Aug. 31, 2017

(65) Prior Publication Data

US 2018/0056297 A1    Mar. 1, 2018

(30) Foreign Application Priority Data

Sep. 1, 2016 (EP) .................................... 16186823

(51) Int. Cl.
| | |
|---|---|
| *B01L 7/00* | (2006.01) |
| *B01L 9/06* | (2006.01) |
| *C12P 19/34* | (2006.01) |
| *B01L 3/00* | (2006.01) |
| *H01L 23/38* | (2006.01) |

(Continued)

(52) U.S. Cl.
CPC .............. *B01L 7/52* (2013.01); *B01L 3/5085* (2013.01); *B01L 9/06* (2013.01); *C12P 19/34* (2013.01); *H01L 23/38* (2013.01); *H01L 27/16* (2013.01); *H05B 3/10* (2013.01); *B01L 2200/025* (2013.01); *B01L 2300/0829* (2013.01); *B01L 2300/1805* (2013.01); *B01L 2300/1822* (2013.01); *B01L 2300/1894* (2013.01)

(58) Field of Classification Search
CPC .. B01L 7/52; B01L 3/5085; B01L 9/06; B01L 2300/1805; B01L 2300/0829; B01L 2200/025; B01L 2300/1822; B01L 2300/1894; C12P 19/34; H01L 27/16; H01L 23/38
See application file for complete search history.

(56) References Cited

U.S. PATENT DOCUMENTS 6,337,435 B1 * 1/2002 Chu .......................... B01L 7/52
                                                       136/203
7,906,767 B2   3/2011 Furlan et al.
(Continued)

FOREIGN PATENT DOCUMENTS

| | | |
|---|---|---|
| WO | WO2005041314 | 5/2005 |
| WO | WO2012136243 | 10/2012 |

OTHER PUBLICATIONS http://i.stack.imgur.com/JaUZE.jpg.

*Primary Examiner* — Emmanuel Duke
(74) *Attorney, Agent, or Firm* — Pamela C. Ancona

(57) ABSTRACT

An assembly comprising a sample block, a heat sink and at least one electrodeposited thermoelectric element is disclosed. Further, an instrument and a method for performing a temperature-dependent reaction are disclosed.

14 Claims, 6 Drawing Sheets

(51) Int. Cl.
*H01L 27/16* (2006.01)
*H05B 3/10* (2006.01)

(56) References Cited

U.S. PATENT DOCUMENTS

| | | | | |
|---|---|---|---|---|
| 8,151,575 B2* | 4/2012 | Wu | .......... | F25B 21/02 |
| | | | | 165/181 |
| 2004/0149725 A1* | 8/2004 | Brown | ........ | B01L 7/52 |
| | | | | 219/477 |
| 2005/0009070 A1* | 1/2005 | Arciniegas | .......... | B01L 3/50851 |
| | | | | 435/6.11 |
| 2005/0123457 A1* | 6/2005 | Tajima | ........ | B01L 3/50 |
| | | | | 422/130 |
| 2006/0101830 A1* | 5/2006 | Cohen | ...... | F25B 21/04 |
| | | | | 62/3.3 |
| 2007/0003443 A1* | 1/2007 | Sandell | ........ | B01L 3/0275 |
| | | | | 422/400 |
| 2008/0308140 A1 | 12/2008 | Nakamura | | |
| 2011/0165628 A1* | 7/2011 | Verhaar | ........ | B01L 3/50851 |
| | | | | 435/91.2 |
| 2013/0137144 A1* | 5/2013 | Chu | .......... | B01L 7/52 |
| | | | | 435/91.2 |
| 2013/0143272 A1* | 6/2013 | Guo | .......... | B01L 7/52 |
| | | | | 435/91.2 |

* cited by examiner

ASSEMBLY, INSTRUMENT FOR PERFORMING A TEMPERATURE-DEPENDENT REACTION AND METHOD FOR PERFORMING A TEMPERATURE-DEPENDENT REACTION IN AN ASSEMBLY

CROSS-REFERENCE TO RELATED APPLICATIONS

The present application claims the benefit of priority under 35 U.S.C. § 119(a) of EP 16186823.7, filed Sep. 1, 2016, the disclosure of which is incorporated herein by reference in its entirety.

FIELD OF THE DISCLOSURE

The present disclosure relates to an assembly, to an instrument for performing one or more temperature-dependent reactions and to a method for performing a temperature-dependent reaction in an assembly.

BACKGROUND

An assembly in the sense of the present disclosure comprises a sample block, a heat sink and at least one thermoelectric element. Such a sample block is configured to receive at least one and preferably a plurality of sample vessels. The thermoelectric element is designed as a thermoelectric cooler or a thermoelectric heater. A thermoelectric cooler uses the Peltier effect to create a heat flux between the junction of two different types of materials. A Peltier cooler, heater, or thermoelectric heat pump is a solid-state active heat pump which transfers heat from one side of the device to the other, depending on the direction of the current, with consumption of electrical energy. Such an instrument is also called a Peltier device, Peltier heat pump, solid state refrigerator, or thermoelectric cooler. It can be used either for heating or for cooling, although in practice the main application is cooling. In the field of the present disclosure, it is used as a temperature controller that either heats or cools the sample vessel for controlling a temperature-dependent reaction of a sample within the sample vessel. The heat sink is configured to remove excessive heat. The thermoelectric element and the heat sink allow controlled temperature cycles to be applied to a sample for polymerase chain reaction, which is thereby amplified. Particularly, the thermoelectric element and the heat sink allow the detection of a light reaction when excitation light is applied to the sample.

Particularly, standard thermoelectric elements with ceramics as a substrate are widespread and commonly used. Such thermoelectric elements are described in US 2008/0308140 A1.

Using the above-described thermoelectric element provides advantages concerning the handling within such an assembly. Nevertheless, there are still some drawbacks. Particularly, the tolerance for building openings or holes into thermoelectric elements with ceramics as a substrate is strongly limited. Mounting and fixing takes place between different thermoelectric elements resulting in a minimum distance between them. Further, said ceramics substrate is typically planar. They need to be strongly pre-stressed and assembled in a thermal sandwich using a thermal interface material. A thermal interface material is needed because their structure is very rigid. Nowadays standard thermoelectric elements further provide homogeneous power density due to fixed distances between semiconductor legs. The semiconductor legs are produced by cutting the required block sizes from a e.g. Bismuth Telluride ingot (raw material) and soldering them between two ceramic substrates with required electrical circuit layout copper plating. The process and assembly of the semiconductor blocks is mainly manual work. The finished thermoelectric element assembly always shows thermal edge-effects and corner-effects concerning homogeneity of temperature, caused by varying thermal loss due to cold neighborhood and limiting homogenization capacity of heated/cooled interface platen.

It is therefore an objective of the present disclosure to provide an assembly, an instrument for performing a temperature-dependent reaction and a method of performing a temperature-dependent reaction configured to overcome the above drawbacks and allowing an improved temperature control of the reaction.

SUMMARY

The present disclosure provides an assembly comprising a sample block, a heat sink and at least one electrodeposited thermoelectric element, wherein the sample block comprises one or more recesses each configured to receive a sample vessel, wherein the shape of said at least one electrodeposited thermoelectric element is adapted to the shape of said one or more recesses.

In one embodiment, the electrodeposited thermoelectric element is disposed between the sample block and the heat sink. In a specific embodiment, the electrodeposited thermoelectric element contacts one or more of the sample block and the heat sink, and in a further embodiment, the sample block is fixed to the electrodeposited thermoelectric element and the heat sink. The sample block can be fixed to the electrodeposited thermoelectric element and the heat sink by one or more of the following: a positive fit connection, a non-positive fit connection, and an adhesive bond connection.

The disclosure also contemplates a sample block comprising at least one fixture hole, wherein the electrodeposited thermoelectric element comprises at least one first fixture hole and the heat sink comprises at least one additional fixture hole, wherein at least one threaded bolt engages the at least one first fixture hole of the sample block, the at least one first fixture hole of the electrodeposited thermoelectric element and the at least one additional fixture hole of the heat sink.

The disclosure also provides a sample block comprising at least one recess configured to receive a sample vessel, wherein said recess comprises a bottom end and a recess through-hole positioned in the bottom end, wherein the electrodeposited thermoelectric element comprises at least one element through-hole, wherein the heat sink comprises at least one heat sink through-hole, wherein the recess through-hole, the element through-hole of the electrodeposited thermoelectric element and the heat sink through-hole of the heat sink are aligned on a common axis.

In a particular embodiment, the at least one first recess is tapered towards the electrodeposited thermoelectric element, e.g., the recess is conically shaped.

The electrodeposited thermoelectric element can include two or more thermoelectric zones, wherein the two or more thermoelectric zones are individually operable, and optionally comprise identical or different cooling and/or heating power characteristics. In a particular embodiment, each of the two or more thermoelectric zones comprises sub-portions, wherein the sub-portions comprise the same or different cooling and/or heating power characteristics.

Also provided is an instrument for performing a temperature-dependent reaction comprising an assembly as disclosed herein and at least one laboratory device.

Finally, the disclosure provide a method of performing a temperature-dependent reaction in an assembly as disclosed herein, comprising exposing a sample comprised in a sample vessel disposed in a recess of a sample block to one or more specified temperatures by operating the electrodeposited thermoelectric element.

BRIEF DESCRIPTION OF THE FIGURES

Further details of the disclosure may be derived from the following disclosure of specific embodiments. The features of the embodiments may be realized in an isolated way or in any combination. The disclosure is not restricted to the embodiments. The embodiments are schematically depicted in the figures. Identical reference numbers in the figures refer to identical elements or functionally identical elements or elements corresponding to each other with regard to their functions.

DETAILED DESCRIPTION

Figure 2:
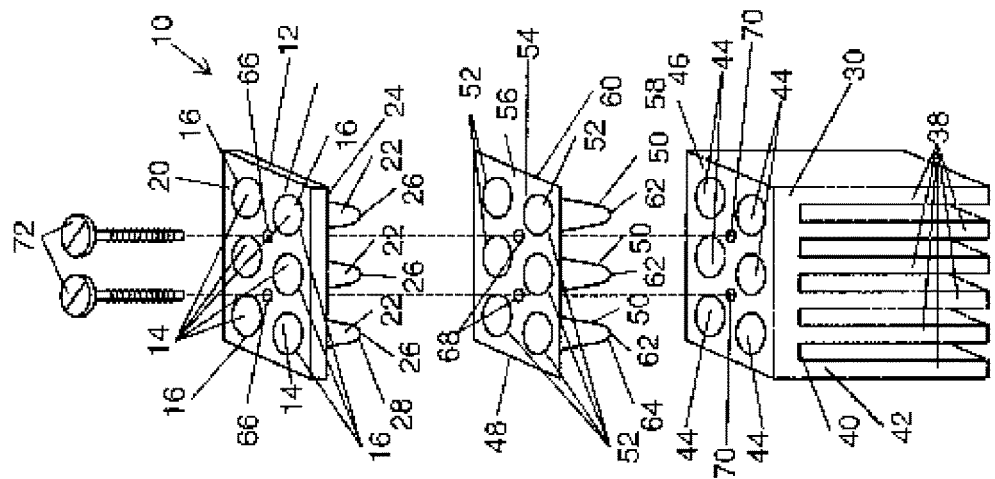
FIG. 2 shows an explosion view of an assembly according to a second embodiment of the present disclosure.

This problem is solved by an assembly, an instrument for performing a temperature-dependent reaction and a method of performing a temperature-dependent reaction with the features of the independent claims. Embodiments, which may be realized in an isolated way or in any arbitrary combination, are listed in the dependent claims.

As used in the following, the terms "have," "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B," "A comprises B" and "A includes B" may both refer to a situation in which, besides B, no other element is present in A (i.e. a situation in which A solely and exclusively consists of B) and to a situation in which, besides B, one or more further elements are present in entity A, such as element C, elements C and D or even further elements.

Further, it shall be noted that the terms "at least one," "one or more" or similar expressions indicating that a feature or element may be present once or more than once typically will be used only once when introducing the respective feature or element. In the following, in most cases, when referring to the respective feature or element, the expressions "at least one" or "one or more" will not be repeated, non-withstanding the fact that the respective feature or element may be present once or more than once.

An assembly is disclosed comprising a sample block, a heat sink and at least one electrodeposited thermoelectric element. Production technology of electro-deposited thermoelectric elements allows for any customized shape such as multiply perforated or recessed thermoelectric elements without loss of applicable power per area. Electro-deposited thermoelectric elements can also be made flexible. They can be brought into many shapes like cylinders or cones. Thus, the production technology of electro-deposited thermoelectric elements allows nearly any thinkable order, shape, layout and size of the particles such as telluride crystals and therefore even makes it possible to provide certain power compensation near the edges and corners.

The electrodeposited thermoelectric element may be disposed between the sample block and the heat sink. Thus, heat may be removed from the sample block and transferred to the heat sink.

The electrodeposited thermoelectric element may contact the sample block and/or the heat sink. Thus, a direct heat transmission from the electrodeposited thermoelectric element to the sample block and/or the heat sink and vice versa is provided.

The sample block may be fixed to the electrodeposited thermoelectric element and the heat sink. Thus, a shift of the sample block relative to the electrodeposited thermoelectric element and the heat sink is prevented. Therefore, the orientation of these constructional members permanently remains the same such the heat flux between these constructional members may be reliably controlled.

For example, the sample block may be fixed to the electrodeposited thermoelectric element and the heat sink by means of a positive fit connection and/or a non-positive fit connection and/or an adhesive bond connection. The adhesive bond connection may be provided by using a thermally stable and thermal conducting glue. Thus, these constructional members may be individually connected to one another depending on the respective shapes and applications.

Particularly, the sample block may comprise at least one fixture bolt. The electrodeposited thermoelectric element may comprise at least one fixture hole and the heat sink may comprise at least one fixture hole. At least one threaded bolt may engage the fixture hole of the thermoelectric element and the fixture hole of the heat sink. Thus, a removable fixation is provided allowing maintenance and exchange of these constructional members.

The sample block may comprise one or more recesses each configured to receive a sample vessel. The shape of said at least one electrodeposited thermoelectric element may be adapted to the shape of said one or more recesses. Thus, it is basically possible to heat and cool several sample vessel mounts with one single electrodeposited thermoelectric element that has a corresponding shape, complicated recesses, holes, craters, through-holes, peninsulas and the like. Using such shaped electrodeposited thermoelectric elements makes it easy to produce directly cooled sample mounts or racks or pucks. For example, the electrodeposited thermoelectric element(s) may be provided as a curved electrodeposited thermoelectric element around a collar of the mount(s).

The sample block may comprise at least one recess configured to receive a sample vessel. The recess may comprise, at its bottom end, a through-hole. The electrodeposited thermoelectric element may comprise at least one through-hole. The heat sink may comprise at least one through-hole. The through-hole of the recess, the through-hole of the electro-deposited thermoelectric cooling element and the through-hole of the heat sink may be aligned on a common axis. Thus, an optical path is provided through which light may propagate and be detected.

The recess may be tapered towards the electrodeposited thermoelectric element. Thus, the thermal interface may be realized in a tapered shape so that pre-load may be realized by reduced spring load and reduced tolerance specifications or for a radial thermal interface where height is a critical design parameter.

For example, the recess may be conically shaped. Thus, the thermal interface may be realized in a conic shape so that pre-load may be realized by reduced spring load and reduced tolerance specifications or for a radial thermal interface where height is a critical design parameter.

The electrodeposited thermoelectric element may comprise thermoelectric zones. The zones are individually operable. Thus, the zones are operable independent on one another. Thus, different heating and/or cooling performances are provided between the respective zones.

The thermoelectric zones may comprise identical or different cooling power or heating power characteristics. Particularly, different zones can be built insulated from each other so that they can be powered independently and differently. That way, thermal homogeneity and/or various ramp or cycling profiles can be reached in one single hardware setup.

Each of the thermoelectric zones may comprise sub-portions. The sub-portions may comprise identical or different cooling power or heating power characteristics. Thus, zones may be divided themselves into sub-portions allowing smaller areas of individual heat transmission. Thus, within one zone, areas or sub-portions with different power characteristics can be implemented to compensate edge effects or design related asymmetries.

The electrodeposited thermoelectric element may basically comprise a planar, ashlar-formed, cylindrical, conical, polygonal, or polygonal with rounded edges shape, polyhedric, polyhedric with rounded edges, or any three dimensional form. Thus, the electro-deposited thermoelectric element may be designed in a plurality of potential shapes. Accordingly, thermoelectric elements made by electrodeposition may be individually shaped with rather low effort.

An instrument for performing a temperature-dependent reaction is disclosed comprising an assembly as described above and at least one laboratory device. Thus, the assembly may be well integrated into different kinds of laboratory instruments.

A method of performing a temperature-dependent reaction in an assembly as described above or an instrument as described above is disclosed. The method comprises exposing a sample comprised in a sample vessel disposed in a recess of a sample block to one or more specified temperatures by operating the electrodeposited thermoelectric element. Thus, the temperature-dependent reaction may be controlled in an improved and simplified manner.

The electrodeposited thermoelectric element may be operated so as to cool and/or heat the sample in the sample vessel. Thus, the temperature within the sample vessel may be controlled by supplying heat to the sample vessel or removing heat from the sample vessel.

A method of determining the presence or absence of an analyte in a sample is disclosed comprising performing the method described above in the presence of a detectable marker which is specific for said analyte, and detecting light emitted by said detectable marker which is indicative of the presence or absence of said analyte. Thus, the individual design of the electro deposited thermoelectric element allows the application within optical detection methods.

The marker may be a fluorophore or an electrochemiluminescent compound. Thus, well established markers may be used with the method.

The marker may be a fluorophore, the sample may be exposed to excitation light during and/or after said temperature-dependent reaction and emitted light may be detected by a detector, wherein said emitted light is indicative for the presence of said analyte. Thus, the analyte may be reliably detected with improved temperature-dependent reaction kinetics.

An excitation light source may be located above the sample block and a detector may be located below the heat sink of the assembly as described above. Thus, the light originating from the sample may be reliably detected in a simple manner.

The term "sample block" as used herein refers to a block shaped constructional member comprising chambers or recesses configured to accommodate sample vessel. The sample vessels may be plastic vessels. Particularly, the sample vessels may be constructed and arranged to permit an optimal heat transfer between the block and a liquid sample comprised within said vessels. This allows for optimal conditions during or after thermocycling and ensures specificity and efficiency of the nucleic acid amplification. The liquid comprises reactants which can be detected by illumination with light beams. Examples of reactants are fluorescent labels which correlate with the formation of a reaction product in the liquid. One example of a reaction is an amplification reaction, such as TMA, NASBA or PCR. Such amplification reactions are well known in the art. Alternatively, the sample vessels are multi well plates, i.e. wells arranged in a microtiter plate.

The term "heat sink" as used herein refers to a passive heat exchanger that transfers the heat generated by an electronic or a mechanical device into a coolant fluid in motion. The transferred heat leaves the device with the fluid in motion, therefore allowing the regulation of the device temperature at physically feasible levels.

The term "electro deposited" as used herein refers to a construction made by electrodeposition. Electro deposition is a processes which includes electrocoating, e-coating, cathodic electrodeposition, anodic electrodeposition, and electrophoretic coating, or electrophoretic painting. A characteristic feature of this process is that colloidal particles suspended in a liquid medium migrate under the influence of an electric field (electrophoresis) and are deposited onto an electrode. All colloidal particles that can be used to form stable suspensions and that can carry a charge can be used in electrophoretic deposition. This includes materials such as polymers, pigments, dyes, ceramics and metals. The process is useful for applying materials to any electrically conductive surface.

The term "positive fit connection" as used herein refers to a connection of at least two elements or constructional members to be connected resulting from an engagement or meshing of these elements. Thereby, these elements may not detach from one another even without force transmission or interruption of the force transmission. With other words, with a positive fit connection one of the elements obstructs the other one or stands in the way thereof. The positive fit connection is also known as positive locking connection.

The term "non-positive fit connection" as used herein refers to a connection of at least two elements or constructional members to be connected resulting from a pressing force that acts perpendicularly to the surfaces of the elements. The elements may not be shifted relative to one another unless the counter force caused by the adhesion force is overcome. The non-positive fit connection is also known as non-positive locking connection.

The term "adhesive bond connection" as used herein refers to a connection of at least two elements or constructional members to be connected resulting from atomic or molecular forces. Such a connection may be provided by applying an intermediate material onto the elements or constructional members to be connected to connect them to one another. The thus produced connections can be soluble or insoluble. The intermediate material may be an adhesive or glue, particularly a thermally stable and thermal conducting glue.

The term "laboratory instrument" as used herein refers to any instrument comprising a detector comprising a light source configured to emit light to samples and a detector configured to detect light emitted from the samples.

The term "light source" as used herein can be any kind of illuminator that can be used for excitation of luminescence generated in a sample to be analyzed. The light source of the present disclosure can be a primary or a secondary light source, wherein a primary light source changes electrical, electromagnetic, chemical, thermal, kinetic or any other form of energy, including e.g. light-emitting diodes based on fluorophores, into light suitable for excitation of a marker molecule in a sample vessel. A secondary light source is a light source which transforms the shape, direction and homogeneity of a light beam into another light beam. It can be a white source or it can only contain a single wavelength, multiple wavelengths or one or more wavelength bands or combinations thereof. Typical light sources are incandescent lamps, gas discharge lamps, or light emitting diodes (LEDs) including organic LEDs (OLEDs). The light source includes illuminants emitting light with a single frequency or with a plurality of different frequencies. Additionally, the light source may be an arrangement of more than one of said illuminants.

The term "detector" as used herein relates to a specific arrangement of a plurality of individual detection sites that are located in the image plane of the image of the field plane. Each individual detection site is a device capable of capturing light and converting the light intensity into a corresponding electrical signal. The image of the fluorescence light originating from each sample contained in a well or vial or sample vessel coincides with at least one detection site. For example, the detector may comprise a charge-coupled device (CCD) chip or a CMOS chip adapted to convert the optical signal transmitted by the light beams into a graphical illustration on a monitor such that the user may recognize the result of his or her measurement.

A non-limiting example of a light source and a detector suitable for use in the embodiments disclosed herein includes reference number 5 and 6, respectively, of EP2148188B1 and the accompanying description, the disclosure of which is incorporated herein by reference in its entirety.

The term "light emitted from the samples or marker" as used herein relates to light beams originating from the samples or marker. These light beams may be luminescence generated by excitation of marker molecules in the samples comprised in the wells or sample vessels, i.e. emission light, or remission light if fluorescent markers are used.

The term "sample", as used herein, refers to a material suspected of containing an analyte of interest. The sample can be derived from any biological source, such as a physiological fluid, including, blood, saliva, ocular lens fluid, cerebral spinal fluid, sweat, urine, milk, ascites fluid, mucous, synovial fluid, peritoneal fluid, amniotic fluid, tissue, cells or the like. The test sample can be pretreated prior to use, such as preparing plasma from blood, diluting viscous fluids, lysis or the like; methods of treatment can involve filtration, distillation, centrifugation, concentration, inactivation of interfering components, and the addition of reagents. A sample may be used directly as obtained from the source or following a pretreatment to modify the character of the sample, e.g. after being diluted with another solution or after having being mixed with reagents e.g. to carry out one or more diagnostic assays like e.g. clinical chemistry assays, immunoassays, coagulation assays, nucleic acid testing, etc. The term "sample" as used herein is therefore not only used for the original sample but also relates to a sample which has already been processed (pipetted, diluted, mixed with reagents, enriched, having been purified, having been amplified etc.). As used herein, the term "analyte" refers to the compound or composition to be detected or measured.

The term "sample vessel" as used herein refers to any kind of container configured to store or accommodate a sample. Thus, the sample vessel may be a tube shaped container, a rack, a puck or a slide.

Summarizing the findings of the present disclosure, the following specific embodiments are disclosed:

Embodiment 1

An assembly comprising a sample block, a heat sink and at least one electrodeposited thermoelectric element.

Embodiment 2

Assembly according to embodiment 1, wherein the electrodeposited thermoelectric element is disposed between the sample block and the heat sink.

Embodiment 3

Assembly according to embodiment 1 or 2, wherein the electrodeposited thermoelectric element contacts the sample block and/or the heat sink.

Embodiment 4

Assembly according to any one of embodiments 1 to 3, wherein the sample block is fixed to the electrodeposited thermoelectric element and the heat sink.

Embodiment 5

Assembly according to any one of embodiments 1 to 4, wherein the sample block is fixed to the electrodeposited thermoelectric element and the heat sink by means of a positive fit connection and/or a non-positive fit connection and/or an adhesive bon connection.

Embodiment 6

Assembly according to any one of embodiments 1 to 5, wherein the sample block comprises at least one fixture hole, wherein the electrodeposited thermoelectric element comprises at least one fixture hole and the heat sink comprises at least one fixture hole, wherein at least one bolt, preferably a threaded bolt, engages the fixture hole of the sample block, the fixture hole of the thermoelectric element and the fixture hole of the heat sink.

Embodiment 7

Assembly according to any one of embodiments 1 to 6, wherein the sample block comprises one or more recesses each configured to receive a sample vessel, wherein the shape of said at least one electrodeposited thermoelectric element is adapted to the shape of said one or more recesses.

Embodiment 8

Assembly according to any one embodiments 1 to 7, wherein the sample block comprises at least one recess configured to receive a sample vessel, wherein said recess comprises, at its bottom end, a through-hole, wherein the electrodeposited thermoelectric element comprises at least one through-hole, wherein the heat sink comprises at least one through-hole, wherein the through-hole of the recess, the through-hole of the electrodeposited thermoelectric cooling element and the through-hole of the heat sink are aligned on a common axis.

Embodiment 9

Assembly according to embodiment 7 or 8, wherein the recess is tapered towards the electrodeposited thermoelectric element.

Embodiment 10

Assembly according to any one of embodiments 7 to 9, wherein the recess is conically shaped.

Embodiment 11

Assembly according to any one of embodiments 1 to 10, wherein the electrodeposited thermoelectric element comprises thermoelectric zones, wherein the zones are individually operable.

Embodiment 12

Assembly according to embodiment 11, wherein the thermoelectric zones comprise identical or different cooling power or heating power characteristics.

Embodiment 13

Assembly according to embodiment 11 or 12, wherein each of the thermoelectric zones comprises sub-portions, wherein the sub-portions comprise identical or different cooling power or heating power characteristics.

Embodiment 14

Assembly according to any one of embodiments 1 to 13, wherein the electrodeposited thermoelectric cooling element comprises a planar, ashlar-formed, cylindrical, conical, polygonal, or polygonal with rounded edges shape, polyhedric, polyhedric with rounded edges, or any three dimensional form.

Embodiment 15

Instrument for performing a temperature-dependent reaction comprising an assembly according to any one of embodiments 1 to 14 and at least one laboratory device.

Embodiment 16

Method of performing a temperature-dependent reaction in an assembly according to any one of embodiments 1 to 14 or an instrument according to embodiment 15, comprising exposing a sample comprised in a sample vessel disposed in a recess of a sample block to one or more specified temperatures by operating the electrodeposited thermoelectric element.

Embodiment 17

Method according to embodiment 16, wherein the electrodeposited thermoelectric element is operated so as to cool and/or heat the sample in the sample vessel.

Embodiment 18

Method of determining the presence or absence of an analyte in a sample comprising performing the method of embodiment 16 in the presence of a detectable marker which is specific for said analyte, and detecting light emitted by said detectable marker which is indicative of the presence or absence of said analyte.

Embodiment 19

Method of embodiment 18, wherein said marker is a fluorophore or an electrochemiluminescent compound.

Embodiment 20

The method of embodiment 19, wherein said marker is a fluorophore, said sample is exposed to excitation light during said temperature-dependent reaction and emitted light is detected by a detector, wherein said emitted light is indicative for the presence of said analyte.

Embodiment 21

The method of embodiment 19, wherein an excitation light source is located above the sample block and a detector is located below the heat sink of the assembly according to embodiment 8 or any embodiment dependent thereon.

Figure 1:
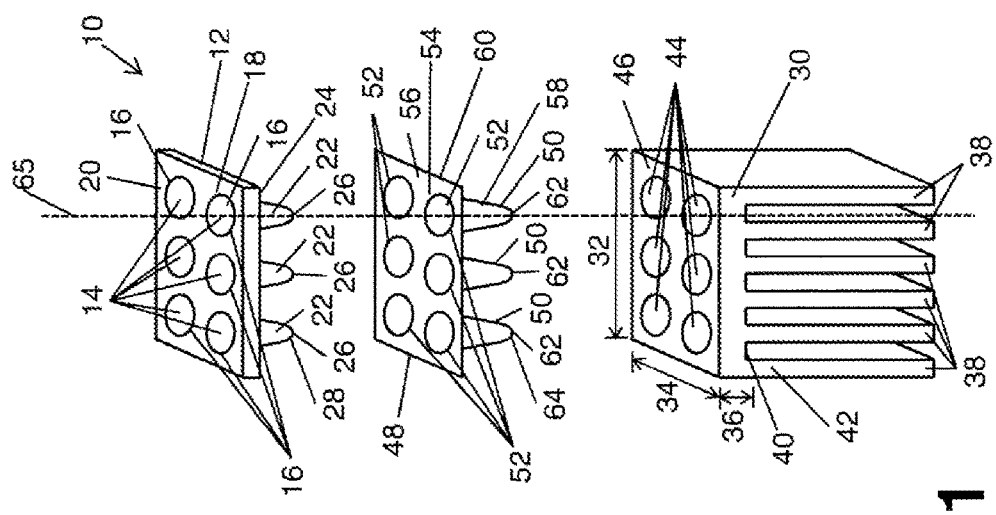
FIG. 1 shows an explosion view of an assembly according to a first embodiment of the present disclosure.

FIG. 1 shows an explosion view of an assembly 10 according to a first embodiment of the present disclosure. The assembly comprises a sample block 12. The sample block 12 is substantially ashlar-formed. The sample block 12 comprises one or more recesses 14. Merely as an example, the sample block 12 is shown so as to comprise six recesses 14 evenly distributed across the sample block 12. More particularly, the recesses 14 are arranged as two parallel rows, wherein each row includes three recesses 14. Needless to say, the sample block 12 may comprise more or less than six recesses 14. Each recess 14 is configured to receive a sample vessel (not shown in detail in FIG. 1). The recesses 14 are conically shaped. Particularly, each recess 14 is shaped such that an orifice 16 at a top end 18 is formed in an upper surface 20 of the sample block 12 and a conical tip 22 protrudes from a lower surface 24 of the sample block 12. Optionally, each recess 14 comprises a through-hole 26 at its bottom end 28.

The assembly 10 further comprises a heat sink 30. The heat sink 30 is substantially ashlar-formed. More particularly, the heat sink 30 comprises a length 32, a width 34 and a height 36. The length 32 is greater than the width 34 which in turn is greater than the height 36. The heat sink 30 comprises one or more fins 38 perpendicularly protruding from a lower surface 40 of the heat sink 30. Merely as an example, the heat sink 30 is shown so as to comprise six fins 38 evenly distributed across the heat sink 30. Needless to say, the heat sink 30 may comprise more or less than six fins 38. The fins 38 are ashlar-formed. Particularly, the fins 38 are arranged parallel to the width 34 and perpendicular to the length 32 of the heat sink 30. The fins 38 are connected to the lower surface 40 at their upper ends 42. For example, the heat sink 30 and the fins 38 are integrally or monolithically formed. The heat sink 30 further comprises six through-holes 44. The through-holes 44 are evenly distributed across the heat sink 30. More particularly, the through-holes 44 are arranged as two parallel rows, wherein each row includes three through-holes 44. The rows extend parallel to the length 32. The through-holes 44 extend from an upper surface 46 of the heat sink 30 and completely extend through the heat sink 30. The through-holes 44 are arranged so as to open out between the fins 38.

The assembly 10 further comprises a thermoelectric element 48. More particularly, the thermoelectric element 48 is an electrodeposited thermoelectric element 48. In other words, the thermoelectric element 48 is made by electrodeposition. The shape of the electrodeposited thermoelectric element 48 is adapted to the shape of the one or more recesses 14 of the sample block 12 as will be explained in further detail below. The electrodeposited thermoelectric element 48 is substantially flat rectangular or thin ashlar-formed. The electrodeposited thermoelectric element 48 comprises one or more hollow protrusions 50. Merely as an example, the electrodeposited thermoelectric element 48 is shown so as to comprise six protrusions 50 evenly distributed across the electrodeposited thermoelectric element 48. Needless to say, the electrodeposited thermoelectric element 48 may comprise more or less than protrusions 50. The protrusions 50 are conically shaped. Particularly, protrusion 50 is shaped such that an orifice 52 at a top end 54 is formed in an upper surface 56 of the electrodeposited thermoelectric element 48 and a conical tip 58 protrudes from a lower surface 60 of the electrodeposited thermoelectric element 48. Optionally, each protrusion 50 comprises a through-hole 62 at its bottom end 64.

Each protrusion 50 of the electrodeposited thermoelectric element 48 is configured to receive a recess 14 of the sample block 12. Further, each through-hole 44 of the heat sink 30 is configured to receive a protrusion 50 of the electrodeposited thermoelectric element 48. The electrodeposited thermoelectric element 48 is disposed between the sample block 12 and the heat sink 30. When mounted, the upper surface 56 of the electrodeposited thermoelectric element 48 faces the lower surface 24 and the lower surface 60 of the electrodeposited thermoelectric element 48 faces the upper surface 46 of the heat sink 30. In this state, the electrodeposited thermoelectric element 48 contacts the sample block 12 and the heat sink 30. Further, each protrusion 50 of the electrodeposited thermoelectric element 48 receives a recess 14 of the sample block 12 and each through-hole 44 of the heat sink 30 receives a protrusion 50 of the electrodeposited thermoelectric element 48. Thus, the sample block 12 is fixed to the electrodeposited thermoelectric element 48 and the heat sink 30 by means of a positive fit connection as they may not be moved laterally to one another, i.e. in a direction parallel to the upper and lower surfaces thereof. As can be further taken from FIG. 1, each through-hole 26 of each recess 14, each through-hole 62 of the electrodeposited thermoelectric element 48 and each through-hole 44 of the heat sink 30 are aligned on a common axis 65. Further, in the mounted state, each recess 14 is tapered towards the electrodeposited thermoelectric element 48.

FIG. 2 shows an explosion view of an assembly 10 according to a second embodiment of the present disclosure. Hereinafter, only the differences from the first embodiment will be explained and like constructional members are indicated by like reference signs. The sample block 12 is fixed to the electrodeposited thermoelectric element 48 and the heat sink 30 by means of a non-positive connection. For this purpose, the sample block 12 comprises at least one fixture hole 66, the electrodeposited thermoelectric element 48 comprises at least one fixture hole 68 and the heat sink 30 comprises at least on fixture hole 70. Merely as an example, respectively two fixture holes 66, 68, 70 are shown arranged between the rows of recesses 14, rows of protrusions 50 and rows of through-holes 44. By means of at least one screw bolt or threaded bolt 72 engaging the fixture holes 66, 68, 70, the sample block, the electrodeposited thermoelectric element 48 and the heat sink 30 are fixed to one another.

Figure 3:
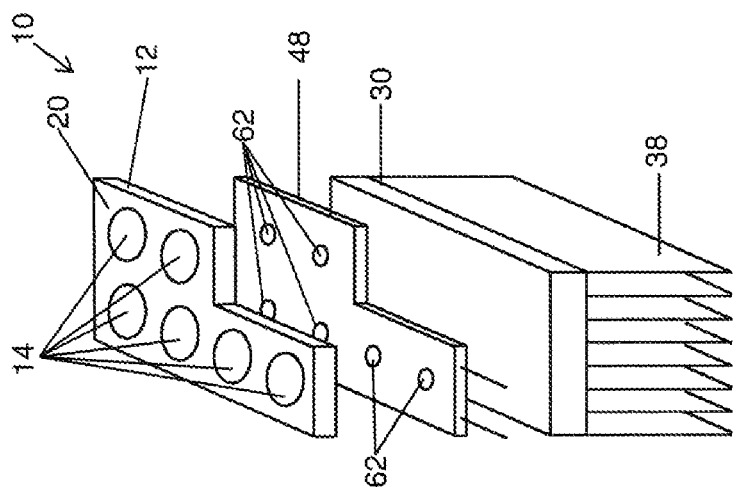
FIG. 3 shows an explosion view of an assembly according to a third embodiment of the present disclosure.

FIG. 3 shows an explosion view of an assembly 10 according to a third embodiment of the present disclosure. Hereinafter, only the differences from the first and second embodiments will be explained and like constructional members are indicated by like reference signs. Basically, the electrodeposited thermoelectric element 48 may comprise a planar, ashlar-formed, cylindrical, conical, polygonal, or polygonal with rounded edges shape, polyhedric, polyhedric with rounded edges, or any three dimensional form. Merely as an example, the electrodeposited thermoelectric element 48 comprises a substantially L-shape if seen in a plan view. The sample block 12 may also comprise a substantially L-shape if seen in a plan view. The heat sink 30 may be formed as described with reference to the first and second embodiments.

Figure 4:
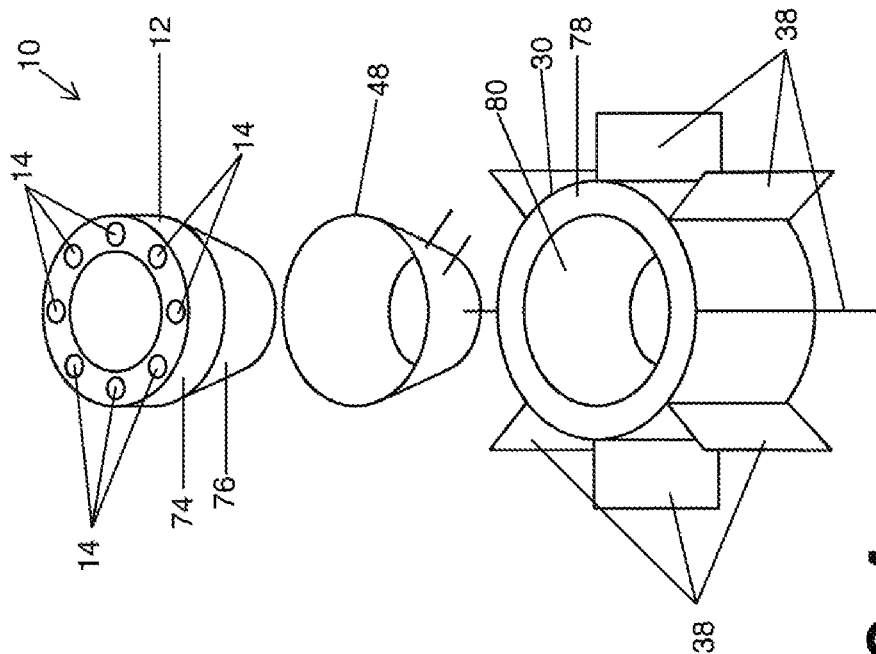
FIG. 4 shows an explosion view of an assembly according to a fourth embodiment of the present disclosure.

FIG. 4 shows an explosion view of an assembly 10 according to a fourth embodiment of the present disclosure. Hereinafter, only the differences from the first to third embodiments will be explained and like constructional members are indicated by like reference signs. The sample block 12 comprises a ring shaped upper portion 74 and a conic lower portion 76. The ring shaped upper portion 74 comprises the through-holes 26. As the shape of the electrodeposited thermoelectric element 48 is also conically shaped and configured to receive and contact the lower portion 76 of the sample block 12. The heat sink 30 comprises a ring shaped or circular outer portion 78 and a conic inner portion 80. The conic inner portion 80 is configured to receive and contact the electrodeposited thermoelectric element 48. Further, the fins 38 are arranged at the outer portion 78 and extend outwardly in a radial direction with respect to the ring shaped or circular outer portion 78.

Figure 5:
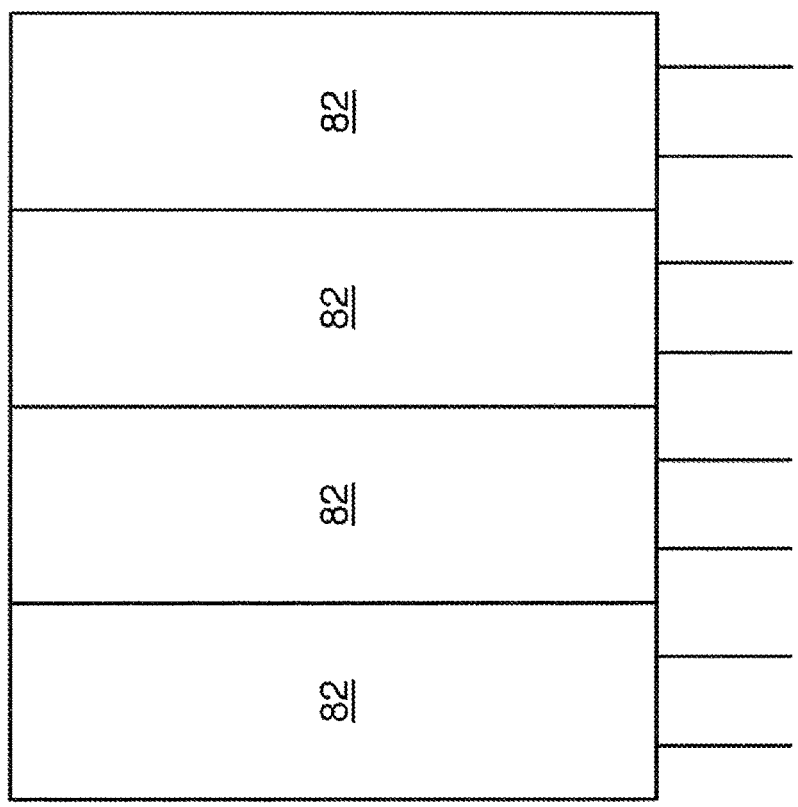
FIG. 5 shows a plan view of an assembly according to a fifth embodiment of the present disclosure.

FIG. 5 shows a plan view of an electrodeposited thermoelectric element 48 according to a fifth embodiment of the present disclosure. Hereinafter, only the differences from the first to fourth embodiments will be explained and like constructional members are indicated by like reference signs. The electrodeposited thermoelectric element 48 may comprise thermoelectric zones 82. Merely as an example, the electrodeposited thermoelectric element 48 is shown so as to comprise four thermoelectric zones 82. Needless to say, the electrodeposited thermoelectric element 48 may comprise more or less than four thermoelectric zones 82. The thermoelectric zones 82 are individually operable. For example, each of the thermoelectric zones 82 may be separately connected to a controllable power source. Alternatively, the thermoelectric zones 82 may be connected to a common control circuit configured to separately operate the thermoelectric zones 82. Thus, each thermoelectric zone 82 may be controlled so as to heat or cool independent on the other thermoelectric zones 82. The thermoelectric zones 82 may comprise identical or different cooling or heating power characteristics. For example, the zones 82 may be arranged so as to dispose a zone 82 having a greater cooling characteristics in contact with a portion of the sample block 12 requiring a greater cooling power to be cooled and to dispose other zones having lees cooling power characteristics in contact with portions of the sample block 12 requiring less cooling power to be cooled. Optionally, the thermoelectric zones 82 may be further divided into sub-portions (not shown in detail). Thereby, each of the thermoelectric zones 82 comprises sub-portions. The sub-portions comprise identical or different cooling power or heating power characteristics. Thus, smaller surface areas may be individually cooled or heated.

Figure 6:
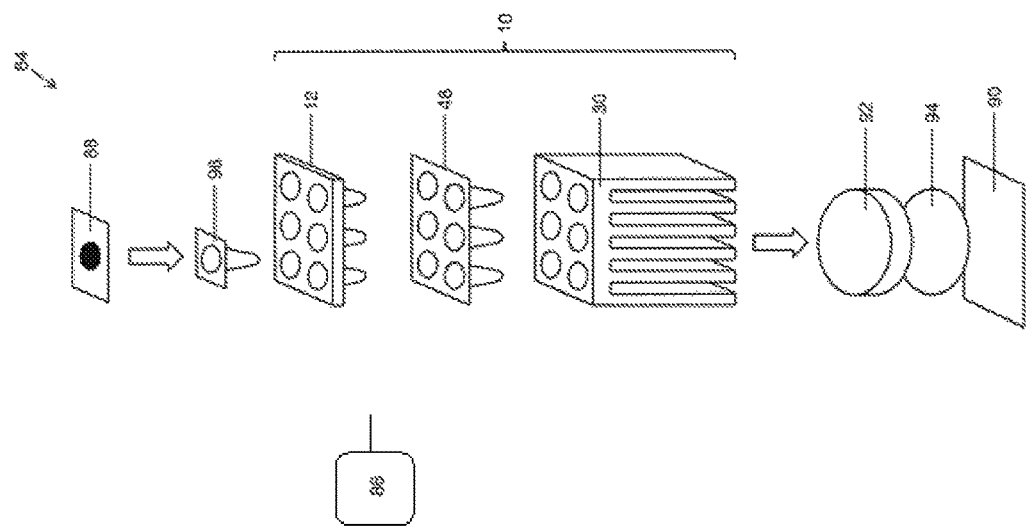
FIG. 6 shows a perspective view of an instrument according to a first embodiment of the present disclosure.

FIG. 6 shows a perspective view of an instrument 84 according to a first embodiment of the present disclosure. The instrument 84 is configured to perform a temperature-dependent reaction as will be explained in further detail below. The instrument 84 comprises an assembly 10 according to any one of the first to fifth embodiments described before. Merely for explaining the basic principle and construction of the instrument 84, the instrument 84 will be described so as to comprise the assembly 10 according to the first embodiment. The instrument 84 further comprises at least one laboratory device 86. The laboratory device 86 comprises a light source 88 and a detector 90. The light source 88 is located above the sample block 12 and faces the upper surface 20 of the sample block 12. The light source 88 is configured to emit excitation light towards the sample block 12. The detector 90 is located below the heat sink 30 and faces the lower surface 40 of the heat sink 30. The detector 90 may be a charge-coupled device sensor, a complementary metal-oxide-semiconductor sensor or the like. Further, optionally, a lens 92 and an optical filter 94 such as an emission band pass filter may be located between the heat sink 30 and the detector 90.

The assembly 10 and the instrument 84, respectively, are used to perform a temperature-dependent reaction. For this purpose, a sample comprised in a sample vessel 96 is disposed in a recess 14 of the sample block 12. The sample is exposed to one or more specified temperatures by operating the electrodeposited thermoelectric element 48. More particularly, the electrodeposited thermoelectric element 48 is operated so as to cool and/or heat the sample in the sample vessel 96. During the temperature-dependent reaction, the presence or absence of an analyte in the sample may be determined. For this purpose, the sample is provided with a detectable marker which is specific for the analyte. The marker is a fluorophore or electrochemiluminescent compound. In the present exemplary embodiment, the marker is a fluorophore. The sample is exposed to excitation light emitted from the light source 88 during the temperature-dependent reaction. The light passes the through-holes 26, 44, 62 of the recess 14, the electrodeposited thermoelectric element 48 and the heat sink 30. Thus, the light also comes into contact with the marker. The light emitted from the marker passes the lens 92 and the optical filter 94 and is subsequently detected by the detector 90. The thus detected light emitted from the marker is indicative of the presence or absence of the analyte.

Figure 7:
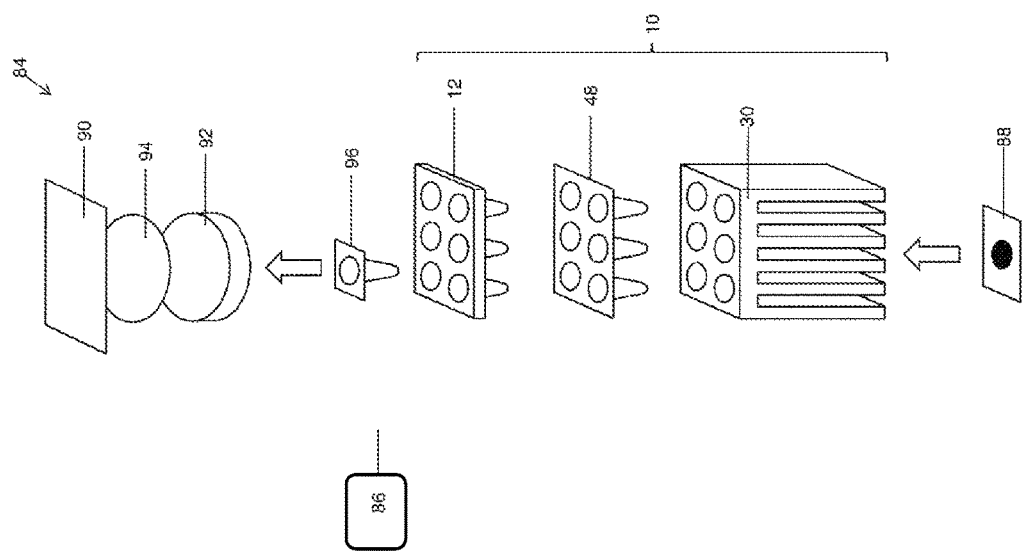
FIG. 7 shows a perspective view of an instrument according to a second embodiment of the present disclosure.

FIG. 7 shows a perspective view of an instrument 84 according to a second embodiment of the present disclosure. Hereinafter, only the differences from the instrument 84 according to the first embodiment will be explained and like constructional members are indicated by like reference signs. Basically, FIG. 7 shows an inverted construction if compared to the instrument 84 of the first embodiment. The light source 88 is located below the heat sink 30 and faces the lower surface 40 of the heat sink 30. The detector 90 is located above the sample block 12 and faces the upper surface 20 of the sample block 12. The lens 92 and the optical filter 94 are located between the sample block 12 and the detector 90. During operation, the light source 88 emits light towards the heat sink 30. The light passes the through-holes 26, 44, 62 of the recess 14, the electrodeposited thermoelectric element 48 and the heat sink 30. Thus, the light also comes into contact with the marker within the sample. The light emitted from the marker passes the lens 92 and the optical filter 94 and is subsequently detected by the detector 90. The thus detected light emitted from the marker is indicative of the presence or absence of the analyte.

Figure 8:
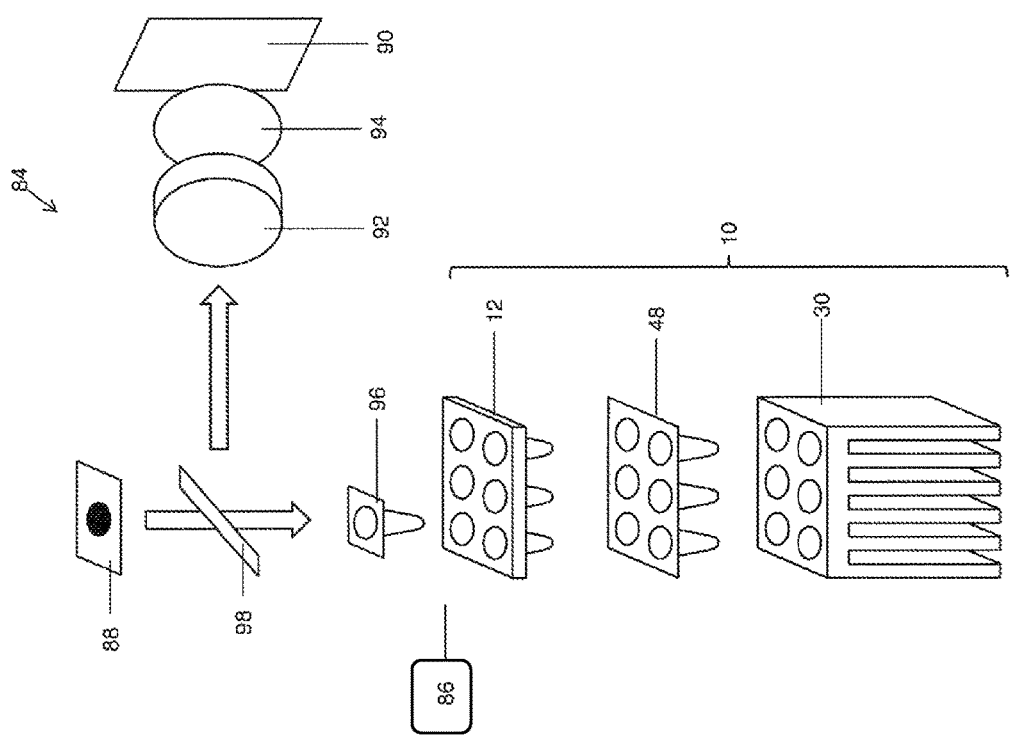
FIG. 8 shows a perspective view of an instrument according to a third embodiment of the present disclosure.

FIG. 8 shows a perspective view of an instrument 84 according to a third embodiment of the present disclosure. Hereinafter, only the differences from the instrument 84 according to the first embodiment will be explained and like constructional members are indicated by like reference signs. The through-holes 26 of the recesses 14 and the through-holes 62 of the electrodeposited thermoelectric element 48 are omitted. A beam splitter 98 is located between the light source 88 and the sample block 12. The lens 92, the optical filter 94 and the detector 90 are also located above the sample block 12 but adjacent to or laterally shifted from the light source 88. The sample is exposed to excitation light emitted from the light source 88 during the temperature-dependent reaction. The light passes the beam splitter 98 and comes into contact the marker within the sample. The light is emitted from the marker in an upward direction, i.e. back towards the light source 88. The light emitted from the marker hits the beam splitter 98 and is reflected towards the lens 92 and the optical filter 94 and is subsequently detected by the detector 90. The thus detected light emitted from the marker is indicative of the presence or absence of the analyte.

The present application is not to be limited in scope by the specific embodiments described herein. Indeed, various modifications in addition to those described herein will become apparent to those skilled in the art from the foregoing description and accompanying figures. Such modifications are intended to fall within the scope of the claims. Various publications are cited herein, the disclosures of which are incorporated by reference in their entireties.

LIST OF REFERENCE NUMBERS 10 assembly
12 sample block
14 recess
16 orifice
18 top end
20 upper surface
22 conical tip 24 lower surface
26 through-hole
28 bottom end
30 heat sink
32 length
34 width
36 height
38 fin
40 lower surface
42 upper end
44 through-hole
46 upper surface
48 electrodeposited thermoelectric element
50 protrusion
52 orifice
54 top end
56 upper surface
58 conical tip
60 lower surface
62 through-hole
64 bottom end
65 common axis
66 fixture hole
68 fixture hole
70 fixture hole
72 threaded bolt
74 upper portion
76 lower portion
78 outer portion
80 inner portion
82 thermoelectric zone
84 instrument
86 laboratory device
88 light source
90 detector
92 lens
94 optical filter
96 sample vessel
98 beam splitter

The invention claimed is:

1. An assembly comprising a sample block, a heat sink and at least one electrodeposited thermoelectric element, wherein the sample block comprises one or more recesses each configured to receive a sample vessel, wherein the shape of said at least one electrodeposited thermoelectric element is adapted to the shape of said one or more recesses.

2. The assembly according to claim 1, wherein the electrodeposited thermoelectric element is disposed between the sample block and the heat sink.

3. The assembly according to claim 1, wherein the electrodeposited thermoelectric element contacts one or more of the sample block and the heat sink.

4. The assembly according to claim 1, wherein the sample block is fixed to the electrodeposited thermoelectric element and the heat sink.

5. The assembly according to claim 1, wherein the sample block is fixed to the electrodeposited thermoelectric element and the heat sink by one or more of the following: a positive fit connection, a non-positive fit connection, and an adhesive bond connection.

6. The assembly according to claim 1, wherein the sample block comprises at least one fixture hole, wherein the electrodeposited thermoelectric element comprises at least one first fixture hole and the heat sink comprises at least one additional fixture hole, wherein at least one threaded bolt engages the at least one first fixture hole of the sample block, the at least one first fixture hole of the electrodeposited thermoelectric element and the at least one additional fixture hole of the heat sink.

7. The assembly according to claim 1, wherein the sample block comprises at least one recess configured to receive the sample vessel, wherein said recess comprises a bottom end and a recess through-hole positioned in the bottom end, wherein the electrodeposited thermoelectric element comprises at least one element through-hole, wherein the heat sink comprises at least one heat sink through-hole, wherein the recess through-hole, the element through-hole of the electrodeposited thermoelectric element and the heat sink through-hole of the heat sink are aligned on a common axis.

8. The assembly according to claim 1, wherein the at least one first recess is tapered towards the electrodeposited thermoelectric element.

9. The assembly according to claim 1, wherein the recess is conically shaped.

10. The assembly according to claim 1, wherein the electrodeposited thermoelectric element comprises two or more thermoelectric zones, wherein the two or more thermoelectric zones are individually operable.

11. The assembly according to claim 10, wherein the two or more thermoelectric zones comprise identical or different cooling and/or heating power characteristics.

12. The assembly according to claim 11, wherein each of the two or more thermoelectric zones comprises sub-portions, wherein the sub-portions comprise the same or different cooling and/or heating power characteristics.

13. The instrument for performing a temperature-dependent reaction comprising an assembly according to claim 1 and at least one laboratory device.

14. A method of performing a temperature-dependent reaction in the assembly according to claim 1, comprising exposing a sample comprised in the sample vessel disposed in a recess of the sample block to one or more specified temperatures by operating the electrodeposited thermoelectric element.

* * * * *